United States Patent
Rao et al.

(10) Patent No.: US 10,351,816 B2
(45) Date of Patent: *Jul. 16, 2019

(54) SIGNAL PEPTIDE, L-GLUTAMIC ACID SYNTHESIZED USING KONJAC FLOUR AND METHODS OF USING SAME

(71) Applicant: Jiangnan University, Wuxi (CN)

(72) Inventors: Zhiming Rao, Wuxi (CN); Zhenghong Xu, Wuxi (CN); Junxian Zheng, Wuxi (CN); Meijuan Xu, Wuxi (CN); Taowei Yang, Wuxi (CN); Xian Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/736,544

(22) PCT Filed: Nov. 23, 2015

(86) PCT No.: PCT/CN2015/095286
§ 371 (c)(1),
(2) Date: Dec. 14, 2017

(87) PCT Pub. No.: WO2017/088095
PCT Pub. Date: Jun. 1, 2017

(65) Prior Publication Data
US 2018/0258385 A1    Sep. 13, 2018

(51) Int. Cl.
| | | |
|---|---|---|
| *C12N 15/09* | (2006.01) |
| *C12N 1/20* | (2006.01) |
| *C12P 13/10* | (2006.01) |
| *C12N 9/24* | (2006.01) |
| *C12N 15/52* | (2006.01) |
| *C07K 14/32* | (2006.01) |
| *C07K 14/34* | (2006.01) |

(52) U.S. Cl.
CPC ............... *C12N 1/20* (2013.01); *C07K 14/32* (2013.01); *C07K 14/34* (2013.01); *C12N 9/2491* (2013.01); *C12N 15/52* (2013.01); *C12P 13/10* (2013.01); *C12Y 302/01025* (2013.01)

(58) Field of Classification Search
None
See application file for complete search history.

(56) References Cited

U.S. PATENT DOCUMENTS

| | | | |
|---|---|---|---|
| 2018/0245114 A1* | 8/2018 | Rao | ........................ C12N 15/77 |
| 2018/0258385 A1* | 9/2018 | Rao | .......................... C12N 1/20 |

OTHER PUBLICATIONS

Tanaka et al. (Biosci., Biotech. & Biochem., vol. 71 (1), 2009, pp. 109-116).*

* cited by examiner

*Primary Examiner* — Hope A Robinson
(74) *Attorney, Agent, or Firm* — Na Xu; IPro, PLLC

(57) ABSTRACT

The present invention relates to application of a novel signal peptide in L-arginine and its derivatives production from konjac powder, which belongs to the field of gene engineering, enzyme engineering and metabolism engineering. The present invention fused the signal peptide set forth in SEQ ID NO.1 with the β-mannanase of *Bacillus subtilis* CCTCC M 209200, and expressed the fused gene in the strain with high L-arginine yield. The recombinant strain *Corynebacterium crenatum* CGMCC 0890/p MSPman had advantages on utilizing cheaper konjac powder as substrate, and after fermenting for 96 hours in a 5 L bioreactor, the L-arginine yield reached 45 g/L. Another two recombinant strains were constructed based on *Corynebacterium crenatum* CGMCC 0890/pMSPman, and after fermenting for 96 hours in a 5 L bioreactor, the L-ornithine yield and L-citrulline reached 23.5 g/L and 26.3 g/L respectively.

1 Claim, No Drawings
Specification includes a Sequence Listing.

SEQUENCE LISTING

<160> NUMBER OF SEQ ID NOS: 11

<210> SEQ ID NO 1
<211> LENGTH: 78
<212> TYPE: DNA
<213> ORGANISM: Artificial Sequence
<220> FEATURE:
<223> OTHER INFORMATION: Synthetic DNA -continued

```
<400> SEQUENCE: 1
atgttcaaga agcacaccat ctccctgctg atcatcttcc tgctggcttc cgctgttctg    60
gctaagccaa tcgaggct                                                  78

<210> SEQ ID NO 2
<211> LENGTH: 78
<212> TYPE: DNA
<213> ORGANISM: Artificial Sequence
<220> FEATURE:
<223> OTHER INFORMATION: Synthetic DNA

<400> SEQUENCE: 2
atgtttaaga acatacgat ctctttgctc attatatttt tacttgcgtc tgctgtttta    60
gcaaaaccaa ttgaagcg                                                  78

<210> SEQ ID NO 3
<211> LENGTH: 1014
<212> TYPE: DNA
<213> ORGANISM: Artificial Sequence
<220> FEATURE:
<223> OTHER INFORMATION: Synthetic DNA

<400> SEQUENCE: 3
atgcatactg tgtcgcctgt gaatcctaat gcccagcaga caacaaaaac agtgatgaac    60
tggcttgcgc acctgccgaa ccgaacggaa acagagtcc tttccggagc gttcggaggt    120
tacagccatg acacattttc tatggctgag gctgatagaa tccgaagcgc cactgggcaa    180
tcgcctgcta tttatggctg cgattatgcc agaggatggc ttgaaacagc aaatattgaa    240
gattcaatag atgtaagctg caacggcgat ttaatgtcgt attggaaaaa tggcggaatt    300
ccgcaaatca gtttgcacct ggcgaacccct gcttttcagt cagggcattt taaaacaccg    360
attacaaatg atcagtataa aaaatactta gattcttcaa cagtagaagg aaggcggcta    420
aatgccatgc tcagcaaaat tgctgacgga cttcaagagt tggagaacca aggtgtgcct    480
gttctgttca ggccgctgca tgaaatgaac ggcgaatggt tttggtgggg actcacatca    540
tataaccaaa aggataatga agaatctct ctatataaac agctctacaa gaaaatctat    600
cattatatga ccgacacaag aggacttgat catttgattt gggtttactc tcccgacgcc    660
aaccgagatt ttaaaactga ttttaccccg ggcgcgtctt acgtggatat tgtcggatta    720
gatgcgtatt ttcaagatgc ctactcgatc aatggatacg atcagctaac agcgcttaat    780
aaaccatttg cttttacaga agtcggcccg caaacagcaa acggcagctt cgattacggc    840
ctgttcatca atgcaataaa acaaaaatat cctaaaacca tttacttcct ggcatggaat    900
gatgaatgga gcgcagcagt aaacaagggt gcttcagctt tatatcatga cagctggaca    960
ctcaacaagg gagaaatatg gaatgatgat tctttaacgc caatcgttga gtaa         1014

<210> SEQ ID NO 4
<211> LENGTH: 109
<212> TYPE: DNA
<213> ORGANISM: Artificial Sequence
<220> FEATURE:
<223> OTHER INFORMATION: Synthetic DNA

<400> SEQUENCE: 4
cccaagctta tgttcaagaa gcacaccatc tccctgctga tcatcttcct gctggcttcc    60
gctgttctgg ctaagccaat cgaggctcat actgtgtcgc ctgtgaatc                109
```

```
<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
cgcggatcct tactcaacga ttggcgtta                                          29

<210> SEQ ID NO 6
<211> LENGTH: 102
<212> TYPE: DNA
<213> ORGANISM: Artificial Sequence
<220> FEATURE:
<223> OTHER INFORMATION: Synthetic DNA

<400> SEQUENCE: 6
atgtttaaca accgtatccg cactgcagct ctcgctggtg caatcgcaat ctccaccgca        60
gcttctggcg tagctatccc agcattcgct caggagacca ct                          102

<210> SEQ ID NO 7
<211> LENGTH: 84
<212> TYPE: DNA
<213> ORGANISM: Artificial Sequence
<220> FEATURE:
<223> OTHER INFORMATION: Synthetic DNA

<400> SEQUENCE: 7
atgtttgcaa aacgattcaa aacctcttta ctgccgttat cgctggatt tttattgctg        60 tttcatttgg ttctggcagg accg                                              84

<210> SEQ ID NO 8
<211> LENGTH: 34
<212> TYPE: DNA
<213> ORGANISM: Artificial Sequence
<220> FEATURE:
<223> OTHER INFORMATION: Synthetic DNA

<400> SEQUENCE: 8
cggaattcat gaaaaaagaa atctcagtta ttgg                                    34

<210> SEQ ID NO 9
<211> LENGTH: 33
<212> TYPE: DNA
<213> ORGANISM: Artificial Sequence
<220> FEATURE:
<223> OTHER INFORMATION: Synthetic DNA

<400> SEQUENCE: 9
ccgagctctt attttagttt ttcaccgaat aaa                                     33

<210> SEQ ID NO 10
<211> LENGTH: 29
<212> TYPE: DNA
<213> ORGANISM: Artificial Sequence
<220> FEATURE:
<223> OTHER INFORMATION: Synthetic DNA

<400> SEQUENCE: 10
ccgagctcat gaagcatccg atacatgtt                                          29

<210> SEQ ID NO 11
<211> LENGTH: 32
<212> TYPE: DNA
```

```
<213> ORGANISM: Artificial Sequence
<220> FEATURE:
<223> OTHER INFORMATION: Synthetic DNA

<400> SEQUENCE: 11
cccaagcttt taaatatctt tacgaacaat tg                              32
```

SIGNAL PEPTIDE, L-GLUTAMIC ACID SYNTHESIZED USING KONJAC FLOUR AND METHODS OF USING SAME

BACKGROUND OF THE INVENTION

Field of the Invention

The invention relates to application of a novel signal peptide in L-arginine and its derivatives production from konjac powder, which belongs to the field of gene engineering, enzyme engineering and metabolism engineering.

Description of the Related Art

Konjac powder, which made from non-grain crops konjac, is rich in konjac mannan. Konjac is mainly distributed in China, Japan, Burma, Vietnam, Indonesia, Southeast Asia and Africa and other regions. Konjac, which belongs to Araceae, is rich in resources, and can be intercropped with food crops, or grown in silt or beaches, thus it doesn't compete arable land with crops, and can be further developed. According to related reports, Yunnan, Guizhou, Sichuan, Hubei and Hunan, Shanxi and other places in the West China are suitable for cultivation of Konjac, there have been certain cultivation scale, and the cultivation area of konjac have reached 410,000 acres in Hubei province. Currently, konjac powder is mainly used for part of food, and its hydrolyzed oligosaccharides can be used as functional food, and its application has not been extensively developed. Konjac, as a main dietary fiber containing food, is identified as one of the top ten health foods by WHO. However, human cannot digest glucomannan from konjac powder, so its daily intake is less than 10 g. A large surplus of konjac can be used for development and utilization. Most microorganisms cannot directly utilize konjac powder, so it has good application prospects to adapt microbes to ferment cheaper konjac powder as a carbon source to produce high-value-added products.

*Corynebacterium crenatum* CGMCC No. 0890 has high yield of L-arginine, which is obtained by multistage mutagenesis, genetic engineering and metabolic engineering technology transformation by our lab. But *Corynebacterium crenatum* CGMCC No. 0890 could only utilize glucose as the main carbon source to produce L-arginine, and konjac powder can't be use as its direct main carbon source.

L-arginine as a semi-essential amino acid is mainly used in the field of pharmaceutical industry, health products, food and so on. By means of genetic and metabolic engineering technique, the high yield strain can also ferment konjac powder as carbon source to produce L-arginine. It has certain reference application value for simplifying the production process of L-arginine and saving the production cost.

L-arginine can be catalyzed by arginase (EC 3.5.3.1) to produce L-ornithine and urea. L-ornithine as a high value-added product derived from L-arginine is a kind of important non-protein amino acids. L-ornithine can promote the synthesis of protein and the catabolism of carbohydrates and lipids, and has an important role in the protection of liver detoxification function.

L-arginine can be catalyzed by Arginine deiminase (EC 3.5.3.6) to produce L-citrulline and ammonia. L-citrulline as a high value-added product derived from L-arginine can be used to maintain pulmonary function, improve mental clarity, enhance memory, relax vascular, enhance male sexual function, as well as treat sexual dysfunction.

The strain which can utilize cheap konjac powder as a carbon source to produce L-arginine is further improved to produce high value-added L-ornithine and L-citrulline through genetical and metabolic engineering technology, and it has considerable prospects to save food and reduce production costs.

DETAILED DESCRIPTION

By taking advantage of genetical engineering, the signal peptide of β-mannanase is deleted from itself first and replaced by 12 new ones from Sec and Tat secreting pathway from *Corynebacterium glutamicum* and *Bacillus subtilis* respectively. The effects of signal peptides replacement on β-mannanase secretion are compared among different strains with high L-arginine production. Finally, the codon of a β-mannanase signal peptide designated as MSP (Mannase Signal Peptide) is optimized which is found to be a new signal peptide with a better enzyme secretion ability.

The first goal of the present invention is to provide a signal peptide, comprises one of the characteristics described as following (a) to (d) items:

(a) the nucleotide sequence of it is the same as the sequence set forth in SEQ ID NO.1;

(b) the nucleotide sequence of it contains the sequence set forth in SEQ ID NO.1, and the signal peptide has an activity of a Mannase signal peptide;

(c) the nucleotide sequence of it contains a sequence which has at least one base of deletion, replacement or addition, compared with the sequence set forth in SEQ ID NO:1; and the signal peptide has an activity of a Mannase signal peptide;

(d) the nucleotide sequence of it is from *Bacillus subtilis*, and could hybridize with the sequence set forth in SEQ ID NO:1 under stringency conditions; and the signal peptide has a activity of Mannase signal peptide.

The second purpose of the present invention is to provide a method of utilizing konjac powder to produce product, the signal peptide is fused with β-mannanase, the expression vector of the fusion protein is introduced to host cell to obtain the recombinant strain, and then use the recombinant strain ferments the konjac powder as a main carbon source.

In one embodiment of the present invention, the gene of the β-mannanase is derived from *Bacillus subtilis*, but not restricted to *Bacillus subtilis*.

In one embodiment of the present invention, the gene of the β-mannanase is derived from *Bacillus subtilis* CCTCC M 209200, the nucleotide sequence is shown in SEQ ID NO:3.

In one embodiment of the present invention, the recombinant strain can produce L-arginine, L-ornithine, or L-citrulline.

In one embodiment of the present invention, the host strain is *Corynebacterium crenatum*, but not restricted to *Corynebacterium crenatum*.

In one embodiment of the present invention, the host strain is *Corynebacterium crenatum* CGMCC No. 0890.

In one embodiment of the present invention, the expression vector is pXMJ19, but not restricted to pXMJ19.

In one embodiment of the present invention, the recombinant strain can express arginase gene, the product is L-ornithine.

In one embodiment of the present invention, the arginase gene derived from *Bacillus cereus*, but not restricted to *Bacillus cereus*.

In one embodiment of the present invention, the NCBI number of the arginase gene is NCBI gi:22934680.

In one embodiment of the present invention, the recombinant strain can express arginine deiminase, the product is L-citrulline.

In one embodiment of the present invention, the arginase deiminase gene derived from *Bacillus cereus*, but not restricted to *Bacillus cereus*.

In one embodiment of the present invention, the NCBI number of the arginase deiminase gene is NCBI gi:22939780.

In one embodiment of the present invention, konjac powder and glucose are used as mixed carbon source; the effect of glucose is to accelerate the cell growth during early fermentation phase, konjac powder is used to induce the secretion of β-mannanase which in turn hydrolyzed konjac powder to provide effective carbon source to produce related products.

In one embodiment of the present invention, the fermentation medium contains 10 g/L konjac powder and 50 g/L glucose, and konjac powder is used as a feed in the late fed-batch fermentation process, and the total feed amount of konjac powder is 90 g/L.

The third purpose of the present invention is to provide a *Corynebacterium crenatum* recombinant strain, the recombinant strain expressed the β-mannanase fused with signal peptide whose nucleotide sequence is set forth in SEQ ID NO:1; after the signal peptide is fused with β-mannanase, the expression vector of the fusion protein is introduced to host cell.

In one embodiment of the present invention, the recombinant strain is named of CGMCC 0890/pMSPman, and it is constructed by the following method: β-mannanase of *Bacillus subtilis* CCTCC M 209200 is fused with the signal peptide, then gene of the fused protein is inserted into pXMJ19 expression vector to form recombinant plasmid named of pXMJ19-MSPman, finally the pXMJ19-MSPman recombinant plasmid is translated to *Corynebacterium crenatum* CGMCC 0890 to get recombinant strain CGMCC 0890/pMSPman.

In one embodiment of the present invention, the recombinant strain is named of CGMCC 0890/pMSPman-padi, and it is constructed by the following method: connect the padi of *Bacillus cereus* to the vector pDXW10, and introduce the expression vector to host cellCGMCC 0890/pMSPman.

In the present invention, a new signal peptide which mediated secretion of β-mannanase is invented, and the recombinant strain with this signal peptide has advantages on utilizing konjac powder to produce related products, and its utilization efficiency of konjac powder, production efficiency, and yield are higher than other signal peptides. The recombinant strain possessing this new signal peptide has advantages on utilizing cheaper konjac powder as substrate to lower the process costs on L-arginine and its high value-added products.

In the present invention, based on the strains with high L-arginine yield, the new constructed strain possessing signal peptide invented in this invention which mediated β-mannanase secretion can utilize mixed carbon source of konjac powder and glucose to produce L-arginine. *Corynebacterium crenatum* CGMCC 0890/pMSPman is constructed in this invention, after fermenting for 96 hours in a 5 L bioreactor, the L-arginine yield and enzyme activity of β-mannanase can reach 45±0.9 g/L and 1505±5.7 U/mL respectively. The initial culture medium contains 10 g/L konjac powder, 50 g/L glucose, and konjac powder is used as a feed in the later fed-batch fermentation process, and the total feed amount of konjac powder is 90 g/L.

In the present invention, the *Corynebacterium crenatum* CGMCC 0890/pMSPman-pargI which can express arginase is constructed based on *Corynebacterium crenatum* CGMCC 0890/pMSPman. The *Corynebacterium crenatum* CGMCC 0890/pMSPman-pargI can utilize konjac powder and glucose as mixed carbon source to produce L-ornithine. The production of L-ornithine and the enzyme activity of β-mannanase can reach 23.5 g/L and 1610±3.8 U/mL by the fermentation with *Corynebacterium crenatum* CGMCC 0890/pMSPman-pargI in a 5 L bioreactor for 96 hours after process optimization. The initial culture medium contains 10 g/L konjac powder, 50 g/L glucose, and konjac powder is used as a feed in the later fed-batch fermentation process, and the total feed amount of konjac powder is 90 g/L.

In the present invention, the *Corynebacterium crenatum* CGMCC 0890/pMSPman-padi which could express arginine deiminase is constructed based on *Corynebacterium crenatum* CGMCC 0890/pMSPman. The *Corynebacterium crenatum* CGMCC 0890/pMSPman-padi can utilize konjac powder and glucose as mixed carbon source to produce L-citrulline. The production of L-citrulline and the enzyme activity of β-mannanase can reach 26.3 g/L and 1360±6.8 U/mL by the fermentation with *Corynebacterium crenatum* CGMCC 0890/pMSPman-padi in a 5 L bioreactor for 96 hours after process optimization. The initial culture medium contains 10 g/L konjac powder, 50 g/L glucose, and konjac powder is used as a feed in the later fed-batch fermentation process, and the total feed amount of konjac powder is 90 g/L.

EXAMPLES

Material and Methods:

Primers: The fusion primers for the signal peptide and target gene were designed according to the related gene sequences published on NCBI.

The strain construction method: The chromosome DNA was extracted from the related strains as templates, and the PCR was run according to the preliminary design of the primers, amplification conditions and system. The PCR products were purified and recovered by using gel extraction kit, and the recovered products concentration were determined by agarose gel electrophoresis of nucleic acid. The related expression vector and purified PCR products were double-enzyme digested by using the same restriction endonuclease, the enzyme-digested products were tested by agarose gel electrophoresis and recovered by gel extraction kit, and its concentration was determined by ultra-microspectrophotometer. Mixed the enzyme-digested products and the PCR products, and connected them by T4 DNA ligase overnight. The recombinant vector was introduced to *Escherichia coli* BL21 by $CaCl_2$ transformation method, finally *Escherichia coli* BL21 containing recombinant plasmid was constructed. The plasmid was extracted and validated by single and double enzyme-digestion and PCR, finally it was introduced to related strain by electrotransformation method. At last, the recombinant strain was stored at −70° C. with 15% glycerol.

The recombinant strain was inoculated into fresh LB+0.5% Glucose liquid culture medium with 1% inoculum concentration. Then it was transferred to fermentation culture medium which contained konjac powder and glucose as substrate at next day. The fermentation broth was collected at the late growth phase and the concentration of amino acids (L-arginine and related amino acids) were determined by automatic amino acids analyzer. The fermentation medium contained enough nutritional ingredient that was suitable for microorganism growth, and had been optimized.

Example 1: The Primers Design for Signal Peptide Tandem β-Mannanase

P1 and P2 for signal peptide tandem β-mannanase were designed according to the related gene sequences and β-mannanase gene published on NCBI. The sequences of P1 and P2 were shown in SEQ ID NO:4 and SEQ ID NO:5 respectively.

```
P1: pMSPmanHindIIIF
5'-CCCAAGCTTATGTTCAAGAAGCACACCATCTCCCTGCTGATCATCTT

CCTGCTGGCTTCCGCTGTTCTGGCTAAGCCAATCGAGGCTCATACTGTGT

CGCCTGTGAATC-3'

P2: pMSPmanBamHIR
5'-CGCGGATCCTTACTCAACGATTGGCGTTA-3'
```

Example 2: Clone and Replacement of Signal Peptide of β-Mannanase

The chromosome DNA was extracted from *B. subtilis* CCTCC M 209200 as templates.

The PCR primers for signal peptide tandem β-mannanase were designed according to the β-mannanase sequence published on NCBI. MSP (Mannase signal peptide) tandem β-mannanase was achieved by using the chromosome DNA of *B. subtilis* CCTCC M 209200 as template and P1/P2 as primers. The codon of MSP was optimized and whose DNA sequence was shown in SEQ ID NO:1, and the sequence of β-mannanase without signal peptide was shown in SEQ ID NO:3. PCR amplification system (50 μL): 1 μL template, 0.5 μL primers, 4 μL dNTP Mix, 5 μL 10×Ex Taq Buffer, 38.5 μL sterile ddH$_2$O, 0.5 μL Ex Taq DNA polymerase. PCR reaction conditions: Pre-denaturation at 94° C. for 5 minutes for one round; sequential denaturation at 94° C. for 30 seconds, annealing at 56° C. for 30 seconds, and elongation at 72° C. for 90 seconds for 30 rounds; elongation at 72° C. for 10 minutes for one round; 4° C. for 40 minutes for one round. The annealing and elongation temperature should be adjusted according to different primers and genes. PCR products were purified and recovered by gel extraction kit, the purity of products was determined by electrophoresis. The recovered products were stored in 1.5 mL centrifuge tubes at −20° C.

Example 3: The Construction of Recombinant Vector pXMJ19-MSPman

Joined the recovered PCR products in embodiment 2 and cloning vector pMD18-T. The ligation system: 5 μL solution, 4.8 μL target gene, 0.2 μL pMD18-T. The ligation between these two DNA molecules was carried out at 16° C. overnight. The recombinant plasmid was introduced to *E. coli* JM109. Then, *E. coli* JM109 was spread on LB plates containing 100 ug/mL ampicillin and cultured at 37° C. overnight. Individual clonal was picked and inoculated to liquid LB culture medium containing 100 ug/mL ampicillin. After cultivation at 37° C. overnight, the plasmid was extracted outside and named pMD18-T-MSPman. When the validation was successful through PCR and enzyme-digestion, the strain was stored at 70° C. with 15% glycerol.

pMD18-T-MSPman and pXMJ19 were cut by HindIII and BamHI, the products were recovered by gel extraction kit and joined together. Finally, recombinant plasmid called pXMJ19-MSPman was achieved. The validation of the recombinant plasmids was successful through PCR and enzyme-digestion.

Example 4: The Electro-Transfection of *Corynebacterium crenatum* CGMCC No. 0890 with Recombinant Vector pXMJ19-MSPman

*Corynebacterium crenatum* CGMCC No. 0890 was picked up and inoculated into flasks with 10 mL LB liquid culture medium, and was cultured at 30° C. overnight. 100 μL broth was taken from flask and inoculated into culture medium for competent cell, and cultured at 30° C. for 4 hours until OD562 reached about 0.9. The broth was centrifuged in sterile tubes and the supernatant was discarded. Then the pellets were resuspended and centrifuged with 10% glycerol for 3 times. Finally, the competent cells were divided into 1.5 mL centrifuge tubes equally, and 3 uL recombinant plasmid was added into those tubes. The competent cells with recombinant plasmid were subjected to an electric-transfection under the condition of 1800 V and 50 mS. Then the cells were inoculated into fresh LBG culture medium (Medium composition: 0.5% yeast extract, 1% peptone, 1% NaCl, 0.5% glucose), and placed into water bath at 46° C. for 6 minutes, then cultured at 30° C. for 3 hours. Finally, the cells were spread on plates containing chloromycetin and cultured at 30° C. for 64 hours. The single colony was picked and cultivated. Then, the plasmid of single colony was extracted and validated through enzyme-digestion and PCR. The positive recombinant strain was named CGMCC No. 0890/pMSPman and stored at 70° C.

Example 5: The Determination of Enzyme Activity of β-Mannanase Secreted from Recombinant CGMCC No. 0890/pMSPman 2.0 mL 5.0 g/L Locust bean gum substrate solution was added to tubes, then preheated the tubes at 65° C. for 10 minutes. 2.0 mL crude enzyme solution with appropriate concentration was added into tubes, and the reaction was carried out at 65° C. for 10 minutes. 5.0 mL DNS reagent was added immediately into tubes, then shook those tubes for a while. Place those tubes into boring water for 10 minutes, then use ice water to cool down tubes. Water was added to make the liquid volume in the tubes to be 10.0 mL, then shook those tubes for a while. 2.0 mL water was used to replace the crude enzyme as control group. The absorbance at 540 nm was measured to calculate the enzyme activity of β-mannanase according to mannose standard curve. The definition of enzyme activity unit: One unit of enzyme activity of β-mannanase was equal to the enzyme amount needed to produce 1 μmol reducing sugar per minute.

Example 6: Fermentation of Recombinant CGMCC No. 0890/pMSPman

The seed of recombinant CGMCC No. 0890/pMSPman was inoculated to konjac powder medium under the cultivation condition of 30° C. and 600 r/min. 96 hours later, the concentration of L-arginine reached 45±0.9 g/L, and the enzyme activity of β-mannanase was 1505±5.7 U/mL.

Konjac Powder Medium (g/L):

The initial culture medium contains 10 g/L konjac powder, 50 g/L glucose, 8 g/L Yeast powder, 20 g/L $(NH_4)_2SO_4$, 1.5 g/L $KH_2PO_4$, 0.5 g/L $MgSO_4.7H_2O$, 0.02 g/L $FeSO_4.7H_2O$, 0.02 g/L $MnSO_4.H_2O$, 30 g/L $CaCO_3$, and the pH of the liquid medium was between 7.0 to 7.2; After fermenting for 12 hours, konjac powder was fed into broth, and the total feed amount of konjac powder was 90 g/L.

Control Group:

Similar fermentation process of embodiment 1-6 was employed to cultivate the control strain which only differed in signal peptide shown in SEQ ID NO:1 that was replaced by the original one of β-mannanase which was shown in SEQ ID NO:2. The concentration of L-arginine was only 31±3.7 g/L, and the enzyme activity of β-mannanase was 1050±3.8 U/mL in control group.

Similar fermentation process of embodiment 1-6 was employed to cultivate the control strain which only differed in signal peptide shown in SEQ ID NO:1 that was replaced by signal peptide PS (SEQ ID NO:6) of surface proteins from *Corynebacterium glutamicum* or by signal peptide AE (SEQ ID NO:7) of α-amylase from *Bacillus subtilis*. The concentration of L-arginine was 26±1.5 g/L and 23±1.2 g/L respectively, and the enzyme activity of β-mannanase was 867±3.7 U/mL and 732±5.9 U/mL respectively in control groups.

To sum up, by taking advantage of signal peptide (SEQ ID NO:1) of this invention, the capability of utilizing konjac powder to produce products of the recombinant strain was significantly improved than by other signal peptides with 45.2%~96% increase in production and 43%~105% increase in the enzyme activity of β-mannanase.

Example 7: The Determination of L-Arginine of Recombinant CGMCC 0890/pMSPman

L-arginine in the fermentation broth was first determined by reagent method in sakaguchi, Fermented supernatant was diluted 500 times, take 1 mL in the colorimetric tube, added 4 mL 0.375 mol/L NaOH solution, then added 1 mL of chromogenic agent, shook up and then putted it in 30° C. water for 20 minutes, each tube was measured by spectrophotometer at 520 nm absorbance value, according to the standard curve to calculate the L-arginine content in the fermented liquid. Then its accurate concentration was determined by an amino acids analyzer.

Example 8: The Primer Design for Construction of Recombinant CGMCC 0890/pMSPman-pargI Based on the inventors' former patent (Publication Number: CN103243128A), the designed primer p1 and p2 were shown below in SEQ ID NO:8 and SEQ ID NO:9, respectively.

```
p1: pargIEcoRIF
5'-CGGAATTCATGAAAAAAGAAATCTCAGTTATTGG-3' p2: pargISacIR
5'-CCGAGCTCTTATTTTAGTTTTTCACCGAATAAA-3'
```

Example 9: The Construction of Recombinant Plasmid pDXW10-argI argI gene containing restriction enzyme cutting site of EcoRI and SacI was obtained by using *Bacillus cereus* chromosome as template and primers designed in embodiment 8 and purified by related kits. The purified PCR products and expression vector pDXW10 were cut by EcoRI and SacI, then the products were recovered by gel extraction kit. Join the recovered products at 16° C. overnight. The recombinant plasmid was introduced to *E. coli* JM109, then spread the cells on the LB plates containing 100 ug/mL kanamycin, and cultivated at 37° C. overnight. Single colony was picked up and inoculated to 10 mL LB liquid culture medium containing 100 ug/mL kanamycin. Culture the cells at 37° C. overnight, the extract the plasmid named pDXW10-argI out of broths. After the validation was passed through PCR and enzyme-digestion, the strain was stored at −70° C.

Example 10: The Recombinant Plasmid pDXW10-argI was Electro-Transfected to CGMCC 0890/pMSPman CGMCC 0890/pMSPman was used as an original strain for electro-transfection, and the antibiotic screening marker was kanamycin. Embodiment 4 was used as a reference. Finally, recombinant strain CGMCC 0890/pMSPman-pargI was screened out.

Example 11: The Determination of Enzyme Activity of Glutamate Decarboxylase from Recombinant CGMCC 0890/pMSPman-pargI Prepare 0.2 M L-arginine substrate solution (pH 9.0, containing 0.2 M carbonate buffer solution), then 0.9 ml of substrate solution was mixed with 0.1 ml of enzyme solution for reaction at 40° C. for 10 minutes. Diluted the enzyme reaction solution to the corresponding times, then toke 1.0 mL diluted solution to detect the content of L-ornithine with Chinard colorimetric method. One enzyme activity unit was equal to the enzyme amount needed for production of 1 umol L-ornithine per minute.

Example 12: The Fermentation of Recombinant CGMCC 0890/pMSPman-pargI

The seed of recombinant CGMCC 0890/pMSPman-pargI was inoculated to konjac powder medium under the cultivation condition of 30° C. and 600 r/min. 96 hours later, the concentration of L-ornithine reached 23.5 g/L, and the enzyme activity of β-mannanase was 1610±3.8 U/mL.

Konjac Powder Medium (g/L):

The initial culture medium contains 10 g/L konjac powder, 50 g/L glucose, 8 g/L Yeast Powder, 20 g/L $(NH_4)_2SO_4$, 1.5 g/L $KH_2PO_4$, 0.5 g/L $MgSO_4.7H_2O$, 0.02 g/L $MnSO_4.H_2O$, 0.02 g/L $FeSO_4.7H_2O$, 30 g/L $CaCO_3$, and the pH of the liquid medium was between 7.0 to 7.2; After fermenting for 12 hours, konjac powder was fed into broth, and the total feed amount of konjac powder was 90 g/L.

Control Group:

Similar fermentation process was employed to cultivate the control strain which was only differ in signal peptide that shown in SEQ ID NO:1 was replaced by the original one of β-mannanase which was shown in SEQ ID NO:2. The concentration of L-ornithine was 21±0.8 g/L, and the enzyme activity of β-mannanase was 1025±5.8 U/mL in control group.

Similar fermentation process was employed to cultivate the control strain which was only differ in signal peptide that shown in SEQ ID NO:1 was replaced by signal peptide PS (SEQ ID NO:6) of surface proteins from *Corynebacterium*

*glutamicum* or by signal peptide AE (SEQ ID NO:7) of α-amylase from *Bacillus subtilis*. The concentration of L-ornithine was 17±1.5 g/L and 15±1.3 g/L respectively, and the enzyme activity of β-mannanase was 865±6.7 U/mL and 752±3.9 U/mL respectively in control groups.

To sum up, by taking advantage of signal peptide (SEQ ID NO:1) of this invention, the capability of utilizing konjac powder to produce L-ornithine of the recombinant strain was significantly improved than other signal peptides.

Example 13: The Determination of L-Ornithine from Fermentation Broth of Recombinant CGMCC 0890/pMSPman-pargI Amino acid analyzer was used to determine the precise concentration of L-ornithine from fermentation broth.

Example 14: The Primer Design for Construction of Recombinant CGMCC 0890/pMSPman-padi Based on the inventors' former patent, the designed primer p3 and p4 were shown below in SEQ ID NO:10 and SEQ ID NO:11, respectively.

```
P3: padiSacIF
5'-CCGAGCTCATGAAGCATCCGATACATGTT-3'

P4: psdiHindIIIR
5'-CCCAAGCTTTTAAATATCTTTACGAACAATTG-3'
```

Example 15: The Construction of Recombinant Plasmid pDXW10-adi

The primer was shown in example 14, and the operation was shown in example 9.

Example 16: The Recombinant Plasmid pDXW10-Adi was Electro-Transfected to CGMCC 0890/pMSPman CGMCC 0890/pMSPman was used as an original strain for electro-transfection, and the antibiotic screening marker was kanamycin. Embodiment 4 was used as a reference. Finally, recombinant strain CGMCC 0890/pMSPman-padi was screened out.

Example 17: The Determination of Enzyme Activity of Glutamate Decarboxylase from Recombinant CGMCC 0890/pMSPman-padi Prepare 0.2 M L-arginine substrate solution (pH 9.0, containing 0.2 M carbonate buffer solution), then 0.9 ml of substrate solution was mixed with 0.1 ml of enzyme solution for reaction at 40° C. for 10 minutes. Diluted the enzyme reaction solution to the corresponding times, then toke 1.0 mL diluted solution to detect the content of L-citrulline with Amino acid analyzer. One enzyme activity unit was equal to the enzyme amount needed for production of 1 umol L-citrulline per minute.

Example 18: The Fermentation of Recombinant CGMCC 0890/pMSPman-padi

The seed of recombinant CGMCC 0890/pMSPman-padi was inoculated to konjac powder medium under the cultivation condition of 30° C. and 600 r/min. 96 hours later, the concentration of L-ornithine reached 26.3 g/L, and the enzyme activity of β-mannanase was 1360±6.8 U/mL.

Konjac Powder Medium (g/L):

The initial culture medium contains 10 g/L konjac powder, 50 g/L glucose, 8 g/L Yeast Powder, 20 g/L $(NH_4)_2SO_4$, 1.5 g/L $KH_2PO_4$, 0.5 g/L $MgSO_4.7H_2O$, 0.02 g/L $MnSO_4.H_2O$, 0.02 g/L $FeSO_4.7H_2O$, 30 g/L $CaCO_3$, and the pH of the liquid medium was between 7.0 to 7.2; After fermenting for 12 hours, konjac powder was fed into broth, and the total feed amount of konjac powder was 90 g/L.

Control Group:

Similar fermentation process was employed to cultivate the control strain which was only differ in signal peptide that shown in SEQ ID NO:1 was replaced by the original one of β-mannanase which was shown in SEQ ID NO:2. The concentration of L-citrulline was 22±0.9 g/L, and the enzyme activity of β-mannanase was 1002±4.7 U/mL in control group.

Similar fermentation process was employed to cultivate the control strain which was only differ in signal peptide that shown in SEQ ID NO:1 was replaced by signal peptide PS (SEQ ID NO:6) of surface proteins from *Corynebacterium glutamicum* or by signal peptide AE (SEQ ID NO:7) of α-amylase from *Bacillus subtilis*. The concentration of L-citrulline was 19±1.3 g/L and 16±0.7 g/L respectively, and the enzyme activity of β-mannanase was 832±7.7 U/mL and 763±6.9 U/mL respectively in control groups.

To sum up, by taking advantage of signal peptide (SEQ ID NO:1) of this invention, the capability of utilizing konjac powder to produce L-citrulline of the recombinant strain was significantly improved than other signal peptides.

Example 19: The Determination of L-Ornithine from Fermentation Broth of Recombinant CGMCC 0890/pMSPman-padi Amino acid analyzer was used to determine the precise concentration of L-citrulline from fermentation broth.

While the present invention has been described in some detail for purposes of clarity and understanding, one skilled in the art will appreciate that various changes in form and detail can be made without departing from the true scope of the invention.

The invention claimed is:

1. A mannase signal peptide that is encoded by a non-naturally occurring nucleotide sequence set forth in SEQ ID NO: 1, wherein the mannase signal peptide mediates secretion of beta-mannase.

* * * * *